United States Patent
Rice et al.

(10) Patent No.: US 6,770,452 B1
(45) Date of Patent: Aug. 3, 2004

(54) METHODS FOR THE IDENTIFICATION OF INHIBITORS OF SERINE ACETYLTRANSFERASE ACTIVITY IN PLANTS

(75) Inventors: John W Rice, Pittsboro, NC (US); Lining Guo, Chapel Hill, NC (US); Keith Davis, Durham, NC (US); Adel Zayed, Durham, NC (US); Robert Ascenzi, Cary, NC (US); Joseph Cameron Mitchell, Chapel Hill, NC (US); Daniel N Riggsbee, Raleigh, NC (US); Douglas Boyes, Chapel Hill, NC (US); Rao Mulpuri, Apex, NC (US); Neil Hoffman, Chapel Hill, NC (US); Susanne Kjemtrup, Chapel Hill, NC (US); Carol Hamilton, Apex, NC (US); Jeffrey Woessner, Hillsborough, NC (US); Jorn Gorlach, Manchester, NJ (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 10/402,818

(22) Filed: Mar. 28, 2003

(51) Int. Cl.[7] .......................... C12Q 1/48; C12N 15/09; C12N 9/10
(52) U.S. Cl. .......................... 435/15; 435/69.2; 435/193
(58) Field of Search .......................... 435/15, 69.2, 193, 435/252.3, 320.1; 536/23.2; 800/300

(56) References Cited

FOREIGN PATENT DOCUMENTS

WO      WO 02/10210      *   2/2002

OTHER PUBLICATIONS

Noji, Masaaki et al., *Serine Acetyltransferase Involved in Cysteine Biosynthesis from Spinach: Molecular Cloning, Characterization and Expression Analysis of cDNA Encoding a Plastidic Isoform.* Plant Cell Physiol, 42(6): 627–634 (2001).

Mino, Koshiki et al., *Increase in the Stability of Serine Acetyltransferase from Escherichia coli Against Cold Inactivation and Proteolysis by Forming a Biendzyme Complex,* Biosci. Biotechnol. Biochem., 65(4), 865–874, 2001.

Urano, Yasuomi et al., *Molecular Cloning and Functional Characterization of cDNAs Encoding Cysteine Synthase and Serine Acetyltransferase That May Be Responsible For High Cellular Cysteine Content in Allium Tuberosum,* Gene, 257(2), 269–277, (2000).

Mino, Koshiki et al., *Characteristics of Serine Acetyltransferase From Escherichia coli Deleting Different Lengths of Amino Acid Residues from the C–Terminus,* Biosci. Biotechnol. Biochem., 64(9) 1874–1880, 2000.

Mino, Koshiki et al., *Effects of Bienzyme Complex Formation of Cysteine Synthetase from Escherichia coli on Some Properties and Kinetics,* Biosci. Biotechnol. Biochem., 64(8), 1628–1640, 2000.

Droux, Michel et al., *Interactions Between Serine Acetyltransferase and O–Acetylserine (Thiol) Lyase in Higher Plants—Structural and Kinetic Properties of the Free and Bound Enzymes,* Eur. J. Biochem., 255, 235–245 (1998).

Noji, Masaaki et al., *Isoform–dependent Differences in Feedback Regulation And Subcellular Localization of Serine Acetyltransferase Involved in Cysteine Biosysynthesis from Arabidopsis thaliana,* The Journal of Biological Chemistry, vol. 273, pp. 32739–32745, Issue of Dec. 4, 1998.

Hindson, VJ et al., *Serine Acetyltransferase from Escherichia coli is a Dimer of Trimers,* The Journal of Biological Chemistry, vol. 275, No. 1, Issue of Jan., pp 461–466, 2000.

Wirtz, Markus et al., *The Cysteine Synthase Complex From Plants,* Eur. J. Biochem, 268, 686–693, 2001.

Harms, Karsten et al., *Expression of a Bacterial Serine Acetyltransferase in Transgenic Potato Plants Leads to Increased Levels of Cysteine and Glutathione,* The Plant Journal, 22(4), 335–343, 2000.

* cited by examiner

Primary Examiner—Tekchand Saidha
(74) Attorney, Agent, or Firm—Laura L. Kiefer; Timothy G. Hofmeyer; Deborah H. Spencer

(57) ABSTRACT

The present inventors have discovered that serine acetyltransferase (SAT) is essential for plant growth. Specifically, the inhibition of SAT gene expression in plant seedlings results in reduced growth and altered pigmentation. Thus, SAT is useful as a target for the identification of herbicides. Accordingly, the present invention provides methods for the identification of herbicides by measuring the activity of an SAT in the presence and absence of a compound, wherein an alteration of SAT activity in the presence of the compound indicates the compound as a candidate for a herbicide.

14 Claims, 1 Drawing Sheet

Acetyl-CoA + L-serine

Serine Acetyltransferase (SAT)

O-acetyl-L-serine + CoA

SEQUENCE LISTING

<160> NUMBER OF SEQ ID NOS: 11

<210> SEQ ID NO 1
<211> LENGTH: 939
<212> TYPE: DNA

<213> ORGANISM: Arabidopsis thaliana

<400> SEQUENCE: 1

```
atgccaccgg ccggagaact ccgacatcaa tctccatcaa aggagaaact atcttccgtt    60
acccaatccg atgaagcaga agcagcgtca gcagcgatat ctgcggcagc tgcagatgcg   120
gaagctgccg gattatggac acagatcaag gcggaagctc gccgtgatgc tgaggcggag   180
ccagctttag ctagctatct atattcgacg attctttctc attcgtctct tgaacgatct   240
atctcgtttc atctaggaaa caagctttgt cctcaacgc ttttatccac acttttatac    300
gatctgttct taaacacttt ttcctccgat ccttctcttc gtaacgccac cgtcgcagat   360
ctacgcgctg ctcgtgttcg tgatcctgct tgtatctcgt tctctcattg tctcctcaat   420
tacaaaggct tcttagctat tcaggcgcat cgtgtatcac acaagctatg gacacaatca   480
cggaagccat tagcattagc tctacactca gaatctccg atgtattcgc tgttgatatc    540
catccagcag cgaagatcgg aaaagggata cttctagacc acgcaaccgg agttgtagtc   600
ggagaaacag cggtgattgg gaacaatgtt tcaatccttc accatgtgac actaggtgga   660
acaggtaaag cttgtggaga tagacatccg aagatcggtg acggttgttt gattggagct   720
ggagcgacta ttcttggaaa tgtgaagatt ggtgcaggtg ctaaagtagg agctggttct   780
gttgtgctga ttgacgtgcc ttgtcgaggt actgcggttg ggaatccggc gagacttgtc   840
ggagggaaag agaagccaac gattcatgat gaggaatgtc ctggagaatc gatggatcat   900
acttcattca tctcggaatg gtcagattac atcatataa                          939
```

<210> SEQ ID NO 2
<211> LENGTH: 312
<212> TYPE: PRT
<213> ORGANISM: Arabidopsis thaliana

<400> SEQUENCE: 2

```
Met Pro Pro Ala Gly Glu Leu Arg His Gln Ser Pro Ser Lys Glu Lys
  1               5                  10                  15

Leu Ser Ser Val Thr Gln Ser Asp Glu Ala Glu Ala Ser Ala Ala
             20                  25                  30

Ile Ser Ala Ala Ala Asp Ala Glu Ala Ala Gly Leu Trp Thr Gln
         35                  40                  45

Ile Lys Ala Glu Ala Arg Arg Asp Ala Glu Ala Glu Pro Ala Leu Ala
 50                  55                  60

Ser Tyr Leu Tyr Ser Thr Ile Leu Ser His Ser Ser Leu Glu Arg Ser
 65                  70                  75                  80

Ile Ser Phe His Leu Gly Asn Lys Leu Cys Ser Ser Thr Leu Ser
                 85                  90                  95

Thr Leu Leu Tyr Asp Leu Phe Leu Asn Thr Phe Ser Ser Asp Pro Ser
                100                 105                 110

Leu Arg Asn Ala Thr Val Ala Asp Leu Arg Ala Ala Arg Val Arg Asp
                115                 120                 125

Pro Ala Cys Ile Ser Phe Ser His Cys Leu Leu Asn Tyr Lys Gly Phe
            130                 135                 140

Leu Ala Ile Gln Ala His Arg Val Ser His Lys Leu Trp Thr Gln Ser
145                 150                 155                 160

Arg Lys Pro Leu Ala Leu Ala Leu His Ser Arg Ile Ser Asp Val Phe
                165                 170                 175

Ala Val Asp Ile His Pro Ala Ala Lys Ile Gly Lys Gly Ile Leu Leu
                180                 185                 190
```

Asp His Ala Thr Gly Val Val Gly Glu Thr Ala Val Ile Gly Asn
          195                 200                 205

Asn Val Ser Ile Leu His His Val Thr Leu Gly Gly Thr Gly Lys Ala
            210                 215                 220

Cys Gly Asp Arg His Pro Lys Ile Gly Asp Gly Cys Leu Ile Gly Ala
225                 230                 235                 240

Gly Ala Thr Ile Leu Gly Asn Val Lys Ile Gly Ala Gly Ala Lys Val
                245                 250                 255

Gly Ala Gly Ser Val Val Leu Ile Asp Val Pro Cys Arg Gly Thr Ala
            260                 265                 270

Val Gly Asn Pro Ala Arg Leu Val Gly Gly Lys Glu Lys Pro Thr Ile
        275                 280                 285

His Asp Glu Glu Cys Pro Gly Glu Ser Met Asp His Thr Ser Phe Ile
    290                 295                 300

Ser Glu Trp Ser Asp Tyr Ile Ile
305                 310

<210> SEQ ID NO 3
<211> LENGTH: 1053
<212> TYPE: DNA
<213> ORGANISM: Arabidopsis thaliana

<400> SEQUENCE: 3

```
atgcaccatc atcatcatca ttcttctggt ctggtgccac gcggttctgg tatgaaagaa      60
accgctgctg ctaaattcga acgccagcac atggacagcc agatctgggt taccatgcca     120
ccggccggag aactccgaca tcaatctcca tcaaaggaga actatcttc cgttacccaa      180
tccgatgaag cagaagcagc gtcagcagcg atatctgcgg cagctgcaga tgcggaagct     240
gccggattat ggacacagat caaggcggaa gctcgccgtg atgctgaggc ggagccagct     300
ttagctagct atctatattc gacgattctt tctcattcgt ctcttgaacg atctatctcg     360
tttcatctag gaaacaagct tgttcctca acgcttttat ccacactttt atacgatctg     420
ttcttaaaca ctttttcctc cgatccttct cttcgtaacg ccaccgtcgc agatctacgc     480
gctgctcgtg ttcgtgatcc tgcttgtatc tcgttctctc attgtctcct caattacaaa     540
ggcttcttag ctattcaggc gcatcgtgta tcacacaagc tatggacaca atcacggaag     600
ccattagcat tagctctaca ctcaagaatc tccgatgtat tcgctgttga tatccatcca     660
gcagcgaaga tcggaaaagg gatacttcta gaccacgcaa ccggagttgt agtcggagaa     720
acagcggtga ttgggaacaa tgtttcaatc cttcaccatg tgacactagg tggaacaggt     780
aaagcttgtg gagatagaca tccgaagatc ggtgacggtt gtttgattgg agctggagcg     840
actattcttg gaaatgtgaa gattggtgca ggtgctaaag taggagctgg ttctgttgtg     900
ctgattgacg tgccttgtcg aggtactgcg gttgggaatc cggcgagact tgtcggaggg     960
aaagagaagc caacgattca tgatgaggaa tgtcctggag aatcgatgga tcatacttca    1020
ttcatctcgg aatggtcaga ttacatcata taa                                 1053
```

<210> SEQ ID NO 4
<211> LENGTH: 350
<212> TYPE: PRT
<213> ORGANISM: Arabidopsis thaliana

<400> SEQUENCE: 4

Met His His His His His Ser Ser Gly Leu Val Pro Arg Gly Ser
1               5                   10                  15

```
Gly Met Lys Glu Thr Ala Ala Ala Lys Phe Glu Arg Gln His Met Asp
             20                  25                  30

Ser Pro Asp Leu Gly Thr Met Pro Ala Gly Glu Leu Arg His Gln
         35                  40                  45

Ser Pro Ser Lys Glu Lys Leu Ser Ser Val Thr Gln Ser Asp Glu Ala
         50                  55                  60

Glu Ala Ala Ser Ala Ala Ile Ser Ala Ala Ala Asp Ala Glu Ala
 65                  70                  75                  80

Ala Gly Leu Trp Thr Gln Ile Lys Ala Glu Ala Arg Arg Asp Ala Glu
                 85                  90                  95

Ala Glu Pro Ala Leu Ala Ser Tyr Leu Tyr Ser Thr Ile Leu Ser His
                100                 105                 110

Ser Ser Leu Glu Arg Ser Ile Ser Phe His Leu Gly Asn Lys Leu Cys
             115                 120                 125

Ser Ser Thr Leu Leu Ser Thr Leu Leu Tyr Asp Leu Phe Leu Asn Thr
         130                 135                 140

Phe Ser Ser Asp Pro Ser Leu Arg Asn Ala Thr Val Ala Asp Leu Arg
145                 150                 155                 160

Ala Ala Arg Val Arg Asp Pro Ala Cys Ile Ser Phe Ser His Cys Leu
                165                 170                 175

Leu Asn Tyr Lys Gly Phe Leu Ala Ile Gln Ala His Arg Val Ser His
             180                 185                 190

Lys Leu Trp Thr Gln Ser Arg Lys Pro Leu Ala Leu Ala Leu His Ser
             195                 200                 205

Arg Ile Ser Asp Val Phe Ala Val Asp Ile His Pro Ala Ala Lys Ile
    210                 215                 220

Gly Lys Gly Ile Leu Leu Asp His Ala Thr Gly Val Val Val Gly Glu
225                 230                 235                 240

Thr Ala Val Ile Gly Asn Asn Val Ser Ile His His Val Thr Leu
                245                 250                 255

Gly Gly Thr Gly Lys Ala Cys Gly Asp Arg His Pro Lys Ile Gly Asp
            260                 265                 270

Gly Cys Leu Ile Gly Ala Gly Ala Thr Ile Leu Gly Asn Val Lys Ile
        275                 280                 285

Gly Ala Gly Ala Lys Val Gly Ala Gly Ser Val Leu Ile Asp Val
            290                 295                 300

Pro Cys Arg Gly Thr Ala Val Gly Asn Pro Ala Arg Leu Val Gly Gly
305                 310                 315                 320

Lys Glu Lys Pro Thr Ile His Asp Glu Glu Cys Pro Gly Glu Ser Met
                325                 330                 335

Asp His Thr Ser Phe Ile Ser Glu Trp Ser Asp Tyr Ile Ile
                340                 345                 350

<210> SEQ ID NO 5
<211> LENGTH: 312
<212> TYPE: PRT
<213> ORGANISM: Arabidpsis thaliana

<400> SEQUENCE: 5

Asp Asp Glu Ser Gly Phe Arg Tyr Met Asn Tyr Phe Arg Tyr Pro Asp
1               5                  10                  15

Arg Ser Ser Phe Asn Gly Thr Gln Thr Lys Thr Leu His Thr Arg Pro
                20                  25                  30

Leu Leu Glu Asp Leu Asp Arg Asp Ala Glu Val Asp Asp Val Trp Ala
```

```
                35                  40                  45
Lys Ile Arg Glu Glu Ala Lys Ser Asp Ile Ala Lys Glu Pro Ile Val
 50                  55                  60
Ser Ala Tyr Tyr His Ala Ser Ile Val Ser Gln Arg Ser Leu Glu Ala
 65                  70                  75                  80
Ala Leu Ala Asn Thr Leu Ser Val Lys Leu Ser Asn Leu Asn Leu Pro
                 85                  90                  95
Ser Asn Thr Leu Phe Asp Leu Phe Ser Gly Val Leu Gln Gly Asn Pro
                100                 105                 110
Asp Ile Val Glu Ser Val Lys Leu Asp Leu Leu Ala Val Lys Glu Arg
                115                 120                 125
Asp Pro Ala Cys Ile Ser Tyr Val His Cys Phe Leu His Phe Lys Gly
130                 135                 140
Phe Leu Ala Cys Gln Ala His Arg Ile Ala His Glu Leu Trp Thr Gln
145                 150                 155                 160
Asp Arg Lys Ile Leu Ala Leu Leu Ile Gln Asn Arg Val Ser Glu Ala
                165                 170                 175
Phe Ala Val Asp Phe His Pro Gly Ala Lys Ile Gly Thr Gly Ile Leu
                180                 185                 190
Leu Asp His Ala Thr Ala Ile Val Ile Gly Glu Thr Ala Val Val Gly
                195                 200                 205
Asn Asn Val Ser Ile Leu His Asn Val Thr Leu Gly Gly Thr Gly Lys
210                 215                 220
Gln Cys Gly Asp Arg His Pro Lys Ile Gly Asp Gly Val Leu Ile Gly
225                 230                 235                 240
Ala Gly Thr Cys Ile Leu Gly Asn Ile Thr Ile Gly Glu Gly Ala Lys
                245                 250                 255
Ile Gly Ala Gly Ser Val Val Leu Lys Asp Val Pro Pro Arg Thr Thr
                260                 265                 270
Ala Val Gly Asn Pro Ala Arg Leu Gly Gly Lys Asp Asn Pro Lys
                275                 280                 285
Thr His Asp Lys Ile Pro Gly Leu Thr Met Asp Gln Thr Ser His Ile
    290                 295                 300
Ser Glu Trp Ser Asp Tyr Val Ile
305                 310

<210> SEQ ID NO 6
<211> LENGTH: 336
<212> TYPE: PRT
<213> ORGANISM: Arabidopsis thaliana

<400> SEQUENCE: 6

Met Ala Ala Cys Ile Asp Thr Cys Arg Thr Gly Lys Pro Gln Ile Ser
 1               5                  10                  15
Pro Arg Asp Ser Ser Lys His His Asp Asp Glu Ser Gly Phe Arg Tyr
                 20                  25                  30
Met Asn Tyr Phe Arg Tyr Pro Asp Arg Ser Ser Phe Asn Gly Thr Gln
                 35                  40                  45
Thr Lys Thr Leu His Thr Arg Pro Leu Leu Glu Asp Leu Asp Arg Asp
 50                  55                  60
Ala Glu Val Asp Asp Val Trp Ala Lys Ile Arg Glu Glu Ala Lys Ser
 65                  70                  75                  80
Asp Ile Ala Lys Glu Pro Ile Val Ser Ala Tyr Tyr His Ala Ser Ile
                 85                  90                  95
```

```
Val Ser Gln Arg Ser Leu Glu Ala Ala Leu Ala Asn Thr Leu Ser Val
            100                 105                 110

Lys Leu Ser Asn Leu Asn Leu Pro Ser Asn Thr Leu Phe Asp Leu Phe
        115                 120                 125

Ser Gly Val Leu Gln Gly Asn Pro Asp Ile Val Glu Ser Val Lys Leu
    130                 135                 140

Asp Leu Leu Ala Val Lys Glu Arg Asp Pro Ala Cys Ile Ser Tyr Val
145                 150                 155                 160

His Cys Phe Leu His Phe Lys Gly Phe Leu Ala Cys Gln Ala His Arg
                165                 170                 175

Ile Ala His Glu Leu Trp Thr Gln Asp Arg Lys Ile Leu Ala Leu Leu
            180                 185                 190

Ile Gln Asn Arg Val Ser Glu Ala Phe Ala Val Asp Phe His Pro Gly
        195                 200                 205

Ala Lys Ile Gly Thr Gly Ile Leu Leu Asp His Ala Thr Ala Ile Val
    210                 215                 220

Ile Gly Glu Thr Ala Val Val Gly Asn Asn Val Ser Ile Leu His Asn
225                 230                 235                 240

Val Thr Leu Gly Gly Thr Gly Lys Gln Cys Gly Asp Arg His Pro Lys
                245                 250                 255

Ile Gly Asp Gly Val Leu Ile Gly Ala Gly Thr Cys Ile Leu Gly Asn
            260                 265                 270

Ile Thr Ile Gly Glu Gly Ala Lys Ile Gly Ala Gly Ser Val Val Leu
        275                 280                 285

Lys Asp Val Pro Pro Arg Thr Thr Ala Val Gly Asn Pro Ala Arg Leu
    290                 295                 300

Leu Gly Gly Lys Asp Asn Pro Lys Thr His Asp Lys Ile Pro Gly Leu
305                 310                 315                 320

Thr Met Asp Gln Thr Ser His Ile Ser Glu Trp Ser Asp Tyr Val Ile
                325                 330                 335
```

<210> SEQ ID NO 7
<211> LENGTH: 294
<212> TYPE: PRT
<213> ORGANISM: Citrullus lanatus

<400> SEQUENCE: 7

```
Met Pro Val Gly Glu Leu Arg Phe Ser Ser Gln Ser Ser Thr Thr Val
1               5                   10                  15

Val Glu Ser Thr Thr Asn Asn Asp Glu Thr Trp Leu Trp Gly Gln Ile
            20                  25                  30

Lys Ala Glu Ala Arg Arg Asp Ala Glu Ser Glu Pro Ala Leu Ala Ser
        35                  40                  45

Tyr Leu Tyr Ser Thr Ile Leu Ser His Ser Ser Leu Glu Arg Ser Leu
    50                  55                  60

Ser Phe His Leu Gly Asn Lys Leu Cys Ser Ser Thr Leu Leu Ser Thr
65                  70                  75                  80

Leu Leu Tyr Asp Leu Phe Leu Asn Ala Phe Ser Thr Asp Tyr Cys Leu
                85                  90                  95

Arg Ser Ala Val Val Ala Asp Leu Gln Ala Ala Arg Glu Arg Asp Pro
            100                 105                 110

Ala Cys Val Ser Phe Ser His Cys Leu Leu Asn Tyr Lys Gly Phe Leu
        115                 120                 125

Ala Cys Gln Ala His Arg Val Ala His Lys Leu Trp Asn Gln Ser Arg
    130                 135                 140
```

```
Arg Pro Leu Ala Leu Ala Leu Gln Ser Arg Ile Ala Asp Val Phe Ala
145                 150                 155                 160

Val Asp Ile His Pro Ala Ala Arg Ile Gly Lys Gly Ile Leu Phe Asp
                165                 170                 175

His Ala Thr Gly Val Val Gly Glu Thr Ala Val Ile Gly Asn Asn
            180                 185                 190

Val Ser Ile Leu His His Val Thr Leu Gly Gly Thr Gly Lys Met Cys
            195                 200                 205

Gly Asp Arg His Pro Lys Ile Gly Asp Gly Val Leu Ile Gly Ala Gly
            210                 215                 220

Ala Thr Ile Leu Gly Asn Val Lys Ile Gly Glu Gly Ala Lys Ile Gly
225                 230                 235                 240

Ala Gly Ser Val Val Leu Ile Asp Val Pro Pro Arg Thr Thr Ala Val
                245                 250                 255

Gly Asn Pro Ala Arg Leu Val Gly Gly Lys Glu Lys Pro Ser Gln Leu
            260                 265                 270

Glu Asp Ile Pro Gly Glu Ser Met Asp His Thr Ser Phe Ile Ser Glu
            275                 280                 285

Trp Ser Asp Tyr Ile Ile
            290

<210> SEQ ID NO 8
<211> LENGTH: 293
<212> TYPE: PRT
<213> ORGANISM: Beta vulgaris

<400> SEQUENCE: 8

Met Pro Gly Gly Glu Val Ser Ala Pro Ser Ser Val Val Leu Pro Thr
1               5                   10                  15

Ala Glu Ser Ile Glu Asn Asp Glu Ala Trp Val Trp Gly Gln Ile Lys
            20                  25                  30

Ala Glu Ala Arg Arg Asp Ala Asp Ser Glu Pro Ala Leu Ala Ser Tyr
        35                  40                  45

Leu Tyr Ser Thr Ile Leu Ser His Ser Ser Leu Glu Arg Ser Leu Ser
50                  55                  60

Phe His Leu Gly Asn Lys Leu Cys Ser Ser Thr Leu Leu Ser Thr Leu
65                  70                  75                  80

Leu Tyr Asp Leu Phe Leu Asn Ile Phe Ser Ser Asp Ser Ser Leu Arg
                85                  90                  95

Val Ala Val Val Ala Asp Leu Arg Ala Ala Arg Val Arg Asp Pro Ala
            100                 105                 110

Cys Val Ser Phe Ser His Cys Leu Leu Asn Tyr Lys Gly Phe Leu Ala
            115                 120                 125

Cys Gln Ala His Arg Val Ala His Arg Leu Trp Asn Gln Glu Arg Gln
130                 135                 140

Pro Leu Ala Leu Ala Leu His Ser Arg Ile Ser Asp Val Phe Ala Val
145                 150                 155                 160

Asp Ile His Pro Ala Ala Arg Ile Gly Lys Ala Ile Leu Phe Asp His
                165                 170                 175

Ala Thr Gly Val Val Ile Gly Glu Thr Ala Val Ile Gly Asp Asn Cys
            180                 185                 190

Ser Ile Leu His His Val Thr Leu Gly Gly Thr Gly Lys Ala Val Gly
            195                 200                 205

Asp Arg His Pro Lys Val Gly Asp Gly Val Leu Ile Gly Ala Gly Ala
```

```
                210                 215                 220
Thr Ile Leu Gly Asn Ile Lys Ile Gly Asp Gly Ala Lys Ile Gly Ala
225                 230                 235                 240

Gly Ser Val Val Leu Ile Asp Val Pro Pro Arg Ala Thr Ala Val Gly
                245                 250                 255

Asn Pro Ala Arg Leu Leu Gly Gly Lys Glu Lys Pro Ser Arg Asn Val
                260                 265                 270

Asp Val Pro Gly Glu Ser Met Asp His Thr Ser Phe Ile Ser Glu Trp
                275                 280                 285

Ser Asp Tyr Ile Ile
    290

<210> SEQ ID NO 9
<211> LENGTH: 30
<212> TYPE: DNA
<213> ORGANISM: synthetic

<400> SEQUENCE: 9
gctcgcggcc gcttatatga tgtaatctga                                    30

<210> SEQ ID NO 10
<211> LENGTH: 27
<212> TYPE: DNA
<213> ORGANISM: synthetic

<400> SEQUENCE: 10
attggtacca tgccaccggc cggagaa                                       27

<210> SEQ ID NO 11
<211> LENGTH: 30
<212> TYPE: DNA
<213> ORGANISM: synthetic

<400> SEQUENCE: 11
gctcgcggcc gcttatatga tgtaatctga                                    30
```

METHODS FOR THE IDENTIFICATION OF INHIBITORS OF SERINE ACETYLTRANSFERASE ACTIVITY IN PLANTS

FIELD OF THE INVENTION

The invention relates generally to plant molecular biology. In particular, the invention relates to methods for the identification of herbicides.

BACKGROUND OF THE INVENTION

The traditional approach to herbicide development may be characterized as "spray and pray". Chemicals produced in milligram or greater quantity are sprayed on plants and then plant growth is monitored. While this strategy has resulted in the identification of commercially important herbicides, cost, efficacy and safety challenge the future productivity of the "spray and pray" method. Accordingly, there is a need to identify herbicide targets so that compound libraries can be screened for herbicidal activity in higher through-put in vitro or cell-based assays. Inhibitors of these targets can then be selected and confirmed as having herbicidal activity in conventional herbicide assays.

Cysteine biosynthesis in plants plays a key role in the sulfur cycle in nature. Cysteine is incorporated into proteins and glutathione or serves as the sulfur donor of methionine and sulfur-containing secondary products in plants. Serine acetyltransferase (SAT) plays a regulatory role in the biosynthesis of cysteine by its property of feedback inhibition by cysteine in bacteria and certain plants. Serine acetyltransferase (EC 2.3.1.30) catalyzes the formation of O-acetyl-L-serine (OAS) from acetyl-CoA and L-serine. The final step of cysteine biosynthesis is the formation of L-cysteine from the substrates O-acetyl-L-serine and sulfide by cysteine synthase (CS).

Three cDNA clones encoding SAT isoforms (SAT-c, SAT-p and SAT-m) have been isolated from *Arabidopsis thaliana*. SAT-c is localized in the cytosol while SAT-p and SAT-m are localized in the chloroplasts and mitochondria respectively. In the case of SAT-c, its activity has been shown to be feedback-inhibited by a low concentration of cysteine (Noji et al. (1998) *J. Biol. Chem.* 273:32739–32745). SAT has two different protein-protein interaction domains. An SAT-SAT domain for homomerization, and also a SAT-CS domain located on the C-terminal portion of the protein for heteromerization. When associated in a complex with CS, SAT has been shown to be activated resulting in higher $V_{max}$ and substrate affinities. The bound CS is also inactivated by this interaction. The resulting product, OAS, then must diffuse out of the complex to be acted upon by free CS and sulfide to form cysteine. The complex itself is stabilized by sulfide (inactivating CS), but OAS helps dissociate the complex (activating CS). Hence, not only is SAT regulated by the formation of cysteine, it is also regulated by protein interactions and additional substrate-product interactions (Wirtz et al. (2001) *Eur. J. Biochem.* 268:686–693).

The present invention discloses SAT as a target for the evaluation of plant growth regulators, especially herbicide compounds, in plants.

SUMMARY OF THE INVENTION

The present inventors have discovered that antisense expression of a SAT cDNA in Arabidopsis causes reduced growth and altered pigmentation. Thus, the present inventors have discovered that SAT is essential for normal plant development and growth, and is useful as a target for the identification of herbicides. Accordingly, in one embodiment the present invention provides methods for the identification of compounds that inhibit SAT expression or activity, comprising: contacting a candidate compound with a SAT and detecting the presence or absence of binding between the compound and the SAT, wherein binding between the compound and the SAT indicates the compound as a herbicide target. In another embodiment of the invention, methods are provided for the identification of compounds that inhibit SAT enzyme activity, comprising: contacting a SAT polypeptide with acetyl-CoA and L-serine in the presence and absence of a compound or contacting a SAT polypeptide with O-acetyl-L-serine and CoA in the presence and absence of a compound; and determining a change in concentration for at least one of acetyl-CoA, L-serine, O-acetyl-L-serine and/or CoA in the presence and absence of the compound, wherein a change in the concentration for any of acetyl-CoA, L-serine, O-acetyl-L-serine and/or CoA indicates that the compound is a candidate herbicide.

DETAILED DESCRIPTION OF THE INVENTION

Definitions

Figure 1:
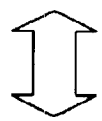
FIG. 1 Diagram of the reversible reaction catalyzed by serine acetyltransferase (SAT). The enzyme catalyzes the reversible interconversion of acetyl-CoA and L-serine to O-acetyl-L-serine and CoA.

The term "bDNA" refers to branched DNA.

The term "binding" refers to a noncovalent interaction that holds two molecules together. For example, two such molecules could be an enzyme and an inhibitor of that enzyme. Noncovalent interactions include hydrogen bonding, ionic interactions among charged groups, van der Waals interactions and hydrophobic interactions among nonpolar groups. One or more of these interactions mediates the binding of two molecules to each other.

As used herein, the term "cDNA" means complementary deoxyribonucleic acid.

As used herein, the term "dI" means deionized.

As used herein, the term "ELISA" means enzyme-linked immunosorbent assay.

As used herein, the term "GUS" means β-glucouronidase.

The term "herbicide", as used herein, refers to a compound useful for killing or suppressing the growth of at least one plant, plant cell, plant tissue or seed.

As used herein, the term "homologous SAT" means either a nucleic acid encoding a polypeptide or a polypeptide, wherein the polypeptide has at least 40%, 45%, 50%, 55%, 60%, 65%, 70%, 75%, 80%, 85%, 90%, 91%, 92%, 93%, 94%, 95%, 96%, 97%, 98%, or 99% sequence identity or each integer unit of sequence identity from 40–100% in ascending order to Arabidopsis SAT protein (SEQ ID NO:2) and at least 10%, 25%, 50%, 75%, 80%, 90%, 95%, or 99% activity or each integer unit of activity from 10–100% in ascending order of the activity of Arabidopsis SAT protein (SEQ ID NO:2). Examples of homologous SAT's include, but are not limited to, SAT from *Citrullus lanatus*, SAT from *Beta vulgaris*, SAT from *Spinacia oleracea*, SAT from

*Nicotiniana tabacum*, SAT from *Allium tuberosum*, SAT from *Allium cepa*, SAT from *Glycine max*, SAT from *Oryza saliva*, and SAT from *Zea mays*.

As used herein, the term "HPLC" means high pressure liquid chromatography.

The term "inhibitor," as used herein, refers to a chemical substance that inactivates the enzymatic activity of SAT or substantially reduces the level of enzymatic activity, wherein "substantially" means a reduction at least as great as the standard deviation for a measurement, preferably a reduction by 50%, more preferably a reduction of at least one magnitude, i.e. to 10%. The inhibitor may function by interacting directly with the enzyme, a cofactor of the enzyme, the substrate of the enzyme, or any combination thereof.

A polynucleotide is "introduced" into a plant cell by any means, including transfection, transformation or transduction, electroporation, particle bombardment, agroinfection and the like. The introduced polynucleotide is maintained in the cell stably if it is incorporated into a non-chromosomal autonomous replicon or integrated into the plant chromosome. Alternatively, the introduced polynucleotide is present on an extra-chromosomal non-replicating vector and be transiently expressed or transiently active.

As used herein, the term "LB" means Luria-Bertani media.

As used herein, the term "Ni-NTA" refers to nickel sepharose.

As used herein, the term "PCR" means polymerase chain reaction.

The "percent (%) sequence identity" between two polynucleotide or two polypeptide sequences is determined according to the either the BLAST program (Basic Local Alignment Search Tool, Altschul and Gish (1996) Meth Enzymol 266: 460–480; Altschul (1990) J Mol Biol 215: 403–410) or using Smith Waterman Alignment (Smith and Waterman (1981) *Adv Appl Math* 2:482) using the default settings and the version current at the time of filing). It is understood that for the purposes of determining sequence identity when comparing a DNA sequence to an RNA sequence, a thymine nucleotide is equivalent to a uracil nucleotide.

"Plant" refers to whole plants, plant organs and tissues (e.g., stems, roots, ovules, stamens, leaves, embryos, meristematic regions, callus tissue, gametophytes, sporophytes, pollen, microspores and the like) seeds, plant cells and the progeny thereof.

By "plant SAT" is meant an enzyme found in at least one plant, and which catalyzes the reversible interconversion of acetyl-CoA and L-serine to O-acetyl-L-serine and CoA. The SAT is from any plant, including monocots, dicots, C3 plants, C4 plants and/or plants that are classified as neither C3 nor C4 plants.

By "polypeptide" is meant a chain of at least four amino acids joined by peptide bonds. The chain is linear, branched, circular or combinations thereof. The polypeptides may contain amino acid analogs and other modifications, including, but not limited to glycosylated or phosphorylated residues.

As used herein, the term "SDS-PAGE" means sodium dodecyl sulfate-polyacrylimide gel electrophoresis.

As used herein, the terms "serine acetyltransferase (SAT)" and "serine acetyltransferase (SAT) polypeptide" refer to an enzyme that catalyzes the reversible interconversion of acetyl-CoA and L-serine to O-acetyl-L-serine and CoA. The terms "serine acetyltransferase (SAT)" and "serine O-acetyltransferase (SAT)" are herein used interchangably.

The term "specific binding" refers to an interaction between SAT and a molecule or compound, wherein the interaction is dependent upon the primary amino acid sequence or the conformation of SAT.

The present inventors have discovered that inhibition of SAT gene expression inhibits the growth and development of plant seedlings. Thus, the inventors are the first to demonstrate that SAT is a useful target for the identification of herbicides.

Accordingly, the invention provides methods for identifying compounds that inhibit SAT protein activity. Such methods include ligand binding assays, assays for enzyme activity and assays for SAT gene expression. The compounds identified by the methods of the invention are useful as herbicides.

Thus, in one embodiment, the invention provides a method for identifying a compound as a candidate for a herbicide, comprising: contacting a SAT with a compound; and detecting the presence and/or absence of binding between the compound and the SAT, wherein binding indicates that the compound is a candidate for a herbicide.

In another embodiment, the invention provides a method for the identification of a compound as a herbicide, comprising: measuring the activity of a SAT in the presence and absence of the compound, wherein an alteration of the SAT activity in the presence of the compound indicates the compound as a candidate for a herbicide.

By "SAT" is meant an enzyme that catalyzes the reversible interconversion of acetyl-CoA and L-serine to O-acetyl-L-serine and CoA. In one embodiment of the invention, the SAT has the amino acid sequence of a naturally occurring SAT found in a plant, animal or microorganism. In another embodiment of the invention, the SAT has an amino acid sequence derived from a naturally occurring sequence. In another embodiment the SAT is a plant SAT. Homologous SAT's are useful in another embodiment of the invention.

One example of a cDNA encoding an *Arabidopsis thaliana* SAT is set forth in SEQ ID NO:1 (TIGR database locus At5g56760). The SAT-52 polypeptide encoded by SEQ ID NO:1 is set forth in SEQ ID NO:2. A nucleic acid molecule encoding an amino-terminal peptide fusion (6-His tag, thrombin cleavage site, S-tag, enterokinase, and Arabidopsis SAT-52, in that order) is set forth in SEQ ID NO:3. The fusion polypeptide encoded by SEQ ID NO:3 is set forth in SEQ ID NO:4. An example of a homologous SAT is an *Arabidopsis thaliana* SAT set forth in SEQ ID NO:5 (Accession NO. CAA58061). Another example of a homologous SAT is an *Arabidopsis thaliana* SAT set forth in SEQ ID NO:6 (Accession NO. CAA56913). Another example of a homologous SAT is a *Citrullus lanatus* SAT set forth in SEQ ID NO:7 (Accession NO. A57478). Another example of a homologous SAT is a Beta vulgaris SAT set forth in SEQ ID NO:8 (Accession NO. CAD67560).

In one embodiment, the SAT is an Arabidopsis SAT. Arabidopsis species include, but are not limited to, *Arabidopsis arenosa, Arabidopsis bursifolia, Arabidopsis cebennensis, Arabidopsis croatica, Arabidopsis griffithiana, Arabidopsis halleri, Arabidopsis himalaica, Arabidopsis korshinskyi, Arabidopsis lyrata, Arabidopsis neglecta, Arabidopsis pumila, Arabidopsis suecica, Arabidopsis thaliana* and *Arabidopsis wallichii*.

In various embodiments, the SAT can be from barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasii*), common lambsquarters (*Chenopodium album* L.), *Brachiara plantaginea, Cassia occidentalis, Ipomoea aristolochiaefolia, Ipomoea purpurea, Euphorbia heterophylia,* Setaria spp, *Amaranthus retroflexus, Sida spinosa, Xanthium strumarium* and the like.

SAT polypeptides having at least 40% sequence identity with Arabidopsis SAT (SEQ ID NO:2) protein are also useful in the methods of the invention. In one embodiment, the sequence identity is at least 40%, 45%, 50%, 55%, 60%, 65%, 70%, 75%, 80%, 85%, 90%, 91%, 92%, 93%, 94%, 95%, 96%, 97%, 98% or 99%, or any integer from 40–100% sequence identity in ascending order with Arabidopsis SAT (SEQ ID) NO:2) protein. In addition, it is preferred that SAT polypeptides of the invention have at least 10% of the activity of Arabidopsis SAT (SEQ ID NO:2) protein. SAT polypeptides of the invention have at least 10%, 15%, 20%, 25%, 30%, 35%, 40%, 45%, 50%, 55%, 60%, 65%, 70%, 75%, 80%, 85% or at least 90% of the activity of Arabidopsis SAT (SEQ ID NO:2) protein.

Polypeptides consisting essentially of SEQ ID NO:2 are also useful in the methods of the invention. For the purposes of the present invention, a polypeptide consisting essentially of SEQ ID NO:2 has at least 90% sequence identity with Arabidopsis SAT (SEQ ID NO:2) and at least 10% of the activity of SEQ ID NO:2. A polypeptide consisting essentially of SEQ ID NO:2 has at least 90%, 91%, 92%, 93%, 94%, 95%, 96%, 97%, 98%, or 99% sequence identity with SEQ ID NO:2 and at least 25%, 50%, 75%, or 90% of the activity of Arabidopsis SAT (SEQ ID NO:2). Examples of polypeptides consisting essentially of SEQ ID NO:2 include, but are not limited to, polypeptides having the amino acid sequence of SEQ ID NO:2 with the exception that one or more of the amino acids are substituted with structurally similar amino acids providing a "conservative amino acid substitution." Conservative amino acid substitutions are well known to those of skill in the art. Particular examples of polypeptides consisting essentially of SEQ ID NO:2 include polypeptides having 1, 2, or 3 conservative amino acid substitutions relative to SEQ ID NO:2.

Other examples of polypeptides consisting essentially of SEQ ID NO:2 include polypeptides having the sequence of SEQ ID NO:2, but with truncations at either or both the 3' and the 5' end. For example, polypeptides consisting essentially of SEQ ID NO:2 include polypeptides having 1, 2, or 3 amino acids residues removed from either or both 3' and 5' ends relative to SEQ ID NO:2. In addition, SAT polypeptides consisting essentially of SEQ ID NO:2 can be fusion proteins, such as SEQ ID NO:4, in which a SAT polypeptide is fused with another polypeptide or amino acid sequence to aid in secretion and/or purification as is known to those of skill in the art.

Fragments of a SAT polypeptide are useful in the methods of the invention. In one embodiment, the SAT fragments include an intact or nearly intact epitope that occurs on the biologically active wild-type SAT. For example, the fragments comprise at least 10 consecutive amino acids of SAT of SEQ ID NO:2. The fragments comprise at least 15, 20, 25, 30, 35, 40, 50, 60, 70, 80, 90, 100, 125, 150, 175, 200, 225, 250, 300 or at least 328 consecutive amino acid residues of SAT of SEQ ID NO:2. In addition, fragments of homologous SAT's are useful in the methods of the invention. Polypeptides comprising at least 50 amino acids having at least 50%, 60%, 70%, 80%, 90%, 95%, 96%, 97%, 98% or 99% sequence identity with at least 50 consecutive amino acid residues of SEQ ID NO:2 are useful in the methods of the invention. In one embodiment, the fragment is from an Arabidopsis SAT. In one embodiment, the fragment contains an amino acid sequence conserved among plant SAT's.

Thus, in another embodiment, the invention provides a method for identifying a compound as a candidate for a herbicide, comprising: contacting a compound with a SAT polypeptide selected from the group consisting of a SAT polypeptide set forth in SEQ ID NO:2 or SEQ ID NO:4; a SAT polypeptide consisting essentially of SEQ ID NO:2; a SAT polypeptide comprising at least 10 consecutive amino acids of SEQ ID NO:2; a SAT polypeptide having at least 50% sequence identity with SEQ ID NO:2; and a polypeptide comprising at least 50 amino acids having at least 50% sequence identity with at least 50 consecutive amino acid residues of SEQ ID NO:2; and detecting the presence and/or absence of binding between the compound and the polypeptide, wherein binding indicates that the compound is a candidate for a herbicide.

Any technique for detecting the binding of a ligand to its target is useful in the methods of the invention. For example, the ligand and target are combined in a buffer. Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with an SAT protein or a homologue, fragment or variant thereof, the unbound protein is removed and the bound SAT is detected. In a preferred embodiment, bound SAT is detected using a labeled binding partner, such as a labeled antibody. In a variation of this assay, SAT is labeled prior to contacting the immobilized candidate ligands. Preferred labels include fluorescent or radioactive moieties. In other embodiments of the invention, detection methods include fluorescence correlation spectroscopy (FCS) and FCS-related confocal nanofluorimetric methods.

In another embodiment of the invention, compounds are tested as candidate herbicides based on ability to inhibit SAT enzyme activity. The compounds are tested using either in vitro or cell based enzyme assays. Alternatively, compounds are tested by direct application to a plant or plant cell, or expressing it therein, and monitoring the plant or plant cell for changes or decreases in growth, development, viability or alterations in gene expression.

A decrease in growth occurs where the herbicide candidate causes at least a 10% decrease in the growth of the plant or plant cells, as compared to the growth of the plants or plant cells in the absence of the herbicide candidate. A decrease in viability occurs where at least 20% of the plants cells, or portions of the plant contacted with the herbicide candidate, are nonviable. Preferably, the growth or viability will be decreased by at least 40%. More preferably, the growth or viability will be decreased by at least 50%, 75%, or at least 90% or more. Methods for measuring plant growth and cell viability are known to those skilled in the art. It is possible that a candidate compound may have herbicidal activity only for certain plants or certain plant species.

The ability of a compound to inhibit SAT activity can be detected using in vitro enzymatic assays in which the disappearance of a substrate or the appearance of a product is directly or indirectly detected. SAT catalyzes the reversible interconversion of acetyl-CoA and L-serine to O-acetyl- L-serine and CoA (see FIG. 1). Methods for measuring the progression of the SAT enzymatic reaction and/or a change in the concentration of the individual reactants acetyl-CoA, L-serine, O-acetyl-L-serine and/or CoA, include spectrophotometry, fluorimetry, mass spectroscopy, thin layer chromatography (TLC) and reverse phase HPLC. Methods for measuring SAT activity are known in the art (e.g. Mino et al. (2001) *Biosci. Biotechnol. Biochem.* 65:865–874. For example, acetyl-CoA absorbs at $A_{232\ nm}$ and its consumption can be followed at that wavelength. One example of a method for the indirect detection of CoA is addition to the enzymatic reaction of a thiol-specific coumarin dye that binds to CoA. Examples of coumarin dyes useful in the methods of the invention include, but are not limited to, 7-diethylamino-3-(4-maleimidylphenyl)-4-methylcoumarin (CPM). Additional methods for the indirect detection of SAT reaction products involve the use of linking enzymes. For example, ninhydrin reagent is used to detect the formation of cysteine when a linked cysteine synthase assay is used to measure activity of the SAT-CS complex. In another example, CoA produced by SAT enzymatic activity is indirectly detected with a ketoglutarate dehydrogenase linking assay. In this embodiment of the invention, ketoglutarate dehydrogenase, ketoglutarate and NAD are added to the SAT enzymatic reaction and the production of CoA is detected through detection of NADH production.

Thus, the invention provides a method for identifying a compound as a candidate herbicide, comprising: contacting acetyl-CoA and L-serine with a SAT in the presence and absence of a compound or contacting O-acetyl-L-serine and CoA with a SAT in the presence and absence of a compound; and determining a change in concentration for at least one of acetyl-CoA, L-serine, O-acetyl-L-serine and/or CoA in the presence and absence of the compound, wherein a change in the concentration for any of the above reactants indicates that the compound is a candidate for a herbicide. In one embodiment of the invention, the SAT is the polypeptide set forth in SEQ ID NO:2. In another embodiment, the SAT is the polypeptide set forth in SEQ ID NO:4. In another embodiment, the SAT is a polypeptide consisting essentially of SEQ ID NO:2. In another embodiment, the SAT is an Arabidopsis SAT polypeptide. In another embodiment, the SAT is a plant SAT. In another embodiment the SAT is a homologous SAT. In another embodiment the SAT is a *Citrullus lanatus* SAT set forth in SEQ ID NO:7. In another embodiment the SAT is a *Beta vulgaris* SAT set forth in SEQ ID NO:8.

Enzymatically active fragments of Arabidopsis SAT set forth in SEQ ID NO:2 are also useful in the methods of the invention. For example, an enzymatically active polypeptide comprising at least 50 consecutive amino acid residues and at least 10% of the activity of Arabidopsis SAT set forth in SEQ ID NO:2 are useful in the methods of the invention. In addition, fragments of homologous SAT's are useful in the methods of the invention. Enzymatically active polypeptides comprising at least 50 amino acids having at least 10% of the activity of SEQ ID NO:2 and at least 50%, 60%, 70%, 80%, 90%, 95%, 96%, 97%, 98% or 99% sequence identity with at least 50 consecutive amino acid residues of SEQ ID NO:2 are useful in the methods of the invention. Most preferably, the enzymatically active polypeptide comprises at least 50 amino acids, has at least 50% sequence identity with at least 50 consecutive amino acid residues of SEQ ID NO:2 and at least 25%, 75% or at least 90% of the activity thereof.

Thus, the invention provides a method for identifying a compound as a candidate herbicide, comprising: contacting acetyl-CoA and L-serine or O-acetyl-L-serine and CoA with a polypeptide selected from the group consisting of: a polypeptide consisting essentially of SEQ ID NO:2, a polypeptide having at least 50% sequence identity with Arabidopsis SAT set forth in SEQ ID NO:2 and having at least 10% of the activity thereof, a polypeptide comprising at least 50 consecutive amino acids of Arabidopsis SAT set forth in SEQ ID NO:3 and having at least 10% of the activity thereof, and a polypeptide comprising at least 50 amino acids, having at least 50% sequence identity with at least 50 consecutive amino acid residues of Arabidopsis SAT set forth in SEQ ID NO:2 and having at least 10% of the activity thereof; contacting acetyl-CoA and L-serine or O-acetyl-L-serine and CoA with the polypeptide and a compound; and determining a change in concentration for at least one of acetyl-CoA, L-serine, O-acetyl-L-serine, and/or CoA in the presence and absence of the compound, wherein a change in concentration for any of the above substances indicates that the compound is a candidate for a herbicide.

For the in vitro enzymatic assays, SAT protein and derivatives thereof may be purified from a plant or may be recombinantly produced in and purified from a plant, bacteria or eukaryotic cell culture. Preferably SAT proteins are produced using a baculovirus, *E. coli* or yeast expression system. Methods for purifying SAT are found, for example, in Droux et al. (1998) *Eur. J Biochem.* 255:235–245 and herein at Example 6. Other methods for the purification of SAT proteins and polypeptides are known to those skilled in the art.

As an alternative to in vitro assays, the invention also provides plant based assays. In one embodiment, the invention provides a method for identifying a compound as a candidate for a herbicide, comprising: a) measuring the expression or activity of a SAT in a plant, or tissue thereof, in the absence of a compound; b) measuring the expression or activity of the SAT in the plant, or tissue thereof, in the presence of the compound; and c) comparing the expression or activity of the SAT in steps (a) and (b), wherein an altered expression or activity in the presence of the compound indicates that the compound is a candidate for a herbicide. In one embodiment, the plant or tissue thereof is *Arabidopsis thaliana*.

In the methods of the invention, expression of a SAT in a plant, or tissue thereof, is measured by detecting the SAT primary transcript or mRNA, SAT polypeptide or SAT enzymatic activity. Methods for detecting the expression of RNA and proteins are known to those skilled in the art. (See, for example, *Current Protocols in Molecular Biology*, Ausubel et al., eds., Greene Publishing and Wiley-Interscience, New York, 1995). However, the method of detection is not critical to the invention. Methods for detecting SAT RNA include, but are not limited to, amplification assays such as quantitative PCR, and/or hybridization assays such as Northern analysis, dot blots, slot blots, in-situ hybridization, transcriptional fusions using an SAT promoter fused to a reporter gene, bDNA assays, and microarray assays.

Methods for detecting protein expression include, but are not limited to, immunodetection methods such as Western blots, His Tag and ELISA assays, polyacrylamide gel electrophoresis, mass spectroscopy, and enzymatic assays. Also, any reporter gene system is useful to detect SAT protein expression. For detection using gene reporter systems, a polynucleotide encoding a reporter protein is fused in frame with SAT, so as to produce a chimeric polypeptide. Methods for using reporter systems are known to those skilled in the art. Examples of reporter genes include, but are not limited to, chloramphenicol acetyltransferase (Gorman et al. (1982) Mol Cell Biol 2: 1104; Prost et al. (1986) Gene 45: 107–111), β-galactosidase (Nolan et al. (1988) Proc Natl Acad Sci USA 85: 2603–2607), alkaline phosphatase (Berger et al. (1988) Gene 66:10), luciferase (De Wet et al. (1987) Mol Cell Biol 7:725–737), β-glucuronidase (GUS), fluorescent proteins, chromogenic proteins and the like. Methods for detecting SAT activity are described above.

Chemicals, compounds, or compositions identified by the above methods as modulators of SAT expression or activity are useful for controlling plant growth. For example, compounds that inhibit plant growth are applied to a plant or expressed in a plant to prevent plant growth. Thus, the invention provides a method for inhibiting plant growth, comprising contacting a plant with a compound identified by the methods of the invention as having herbicidal activity.

Herbicides and herbicide candidates identified by the methods of the invention are useful for controlling the growth of undesired plants, including including monocots, dicots, C3 plants, C4 plants, and plants that are neither C3 nor C4 plants. Examples of undesired plants include, but are not limited, to barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla,* Setaria spp, *Amaranthus retroflexus, Sida spinosa, Xanthium strumarium* and the like.

EXPERIMENTAL

Plant Growth Conditions

Unless, otherwise indicated, all plants were grown in Scotts Metro-Mix™ soil (the Scotts Company) or a similar soil mixture in an environmental growth room at 22° C., 65% humidity, 65% humidity and a light intensity of ~100 $\mu$-E m$^{-2}$ s$^{-1}$ supplied over a 16 hour day period.

Seed Sterilization

All seeds were surface sterilized before sowing onto phytagel plates using the following protocol.
1. Place approximately 20–30 seeds into a labeled 1.5 ml conical screw cap tube. Perform all remaining steps in a sterile hood using sterile technique.
2. Fill each tube with 1 ml 70% ethanol and place on rotisserie for 5 minutes.
3. Carefully remove ethanol from each tube using a sterile plastic dropper; avoid removing any seeds.
4. Fill each tube with 1 ml of 30% Clorox and 0.5% SDS solution and place on rotisserie for 10 minutes.
5. Carefully remove bleach/SDS solution.
6. Fill each tube with 1 ml sterile dI H$_2$O; seeds should be stirred up by pipetting of water into tube. Carefully remove water. Repeat 3 to 5 times to ensure removal of Clorox/SDS solution.
7. Fill each tube with enough sterile dI H$_2$O for seed plating (~200–400 $\mu$l). Cap tube until ready to begin seed plating.

Plate Growth Assays

Surface sterilized seeds were sown onto plate containing 40 ml half strength sterile MS (Murashige and Skoog, no sucrose) medium and 1% Phytagel using the following protocol:
1. Using pipette man and 200 $\mu$l tip, carefully fill tip with seed solution. Place 10 seeds across the top of the plate, about ¼ inch down from the top edge of the plate.
2. Place plate lid ¼ of the way over the plate and allow to dry for 10 minutes.
3. Using sterile micropore tape, seal the edge of the plate where the top and bottom meet.
4. Place plates stored in a vertical rack in the dark at 4° C. for three days.
5. Three days after sowing, the plates were transferred into a growth chamber with a day and night temperature of 22 and 20° C., respectively, 65% humidity and a light intensity of ~100 $\mu$-E m$^{-2}$ s$^{-1}$ supplied over a 16 hour day period.
6. Beginning on day 3, daily measurements are carried out to track the seedlings development until day 14. Seedlings are harvested on day 14 (or when root length reaches 6 cm) for root and rosette analysis.

EXAMPLE 1

Construction of a Transgenic Plant Expressing the Driver

The "Driver" is an artificial transcription factor comprising a chimera of the DNA-binding domain of the yeast GAL4 protein (amino acid residues 1–147) fused to two tandem activation domains of herpes simplex virus protein VP16 (amino acid residues 413–490). Schwechheimer et al. (1998) Plant Mol Biol 36:195–204. This chimeric driver is a transcriptional activator specific for promoters having GAL4 binding sites. Expression of the driver is controlled by two tandem copies of the constitutive CAMV 35S promoter.

The driver expression cassette was introduced into *Arabidopsis thaliana* by agroinfection. Transgenic plants that stably expressed the driver transcription factor were obtained.

EXAMPLE 2

Construction of SAT Antisense Expression Cassettes in a Binary Vector

A fragment of the *Arabidopsis thaliana* cDNA corresponding to SEQ ID NO:1 was ligated into the PacI/AscI sites of an *E.coli*/Agrobacterium binary vector in the antisense orientation to yield an antisense expression cassette and a constitutive chemical resistance expression cassette located between right and left T-DNA borders. In this construct, transcription of the antisense RNA is controlled by an artificial promoter active only in the presence of the driver transcription factor described above. The artificial promoter contains four contiguous binding sites for the GAL4 transcriptional activator upstream of a minimal promoter comprising a TATA box. The ligated DNA was transformed into *E.coli*. Kanamycin resistant clones were selected and purified. DNA was isolated from each clone and characterized by PCR and sequence analysis confirming the presence of the antisense expression cassette.

EXAMPLE 3

Transformation of Agrobacterium with the SAT Antisense Expression Cassette

The binary vector described in Example 2 was transformed into *Agrobacterium tumefaciens* by electroporation. Transformed Agrobacterium colonies were isolated using chemical selection. DNA was prepared from purified resistant colonies and the inserts were amplified by PCR and sequenced to confirm sequence and orientation.

EXAMPLE 4

Construction of Arabidopsis SAT Antisense Target Plants

The SAT antisense expression cassette was introduced into *Arabidopsis thaliana* wild-type plants by the following method. Five days prior to agroinfection, the primary inflorescence of Arabidopsis thaliana plants grown in 2.5 inch pots were clipped to enhance the emergence of secondary bolts.

At two days prior to agroinfection, 5 ml LB broth (10 g/L Peptone, 5 g/L Yeast extract, 5 g/L NaCl, pH 7.0 plus 25 mg/L kanamycin added prior to use) was inoculated with a clonal glycerol stock of Agrobacterium carrying the desired DNA. The cultures were incubated overnight at 28° C. at 250 rpm until the cells reached stationary phase. The following morning, 200 ml LB in a 500 ml flask was inoculated with 500 µl of the overnight culture and the cells were grown to stationary phase by overnight incubation at 28° C. at 250 rpm. The cells were pelleted by centrifugation at 8000 rpm for 5 minutes. The supernatant was removed and excess media was removed by setting the centrifuge bottles upside down on a paper towel for several minutes. The cells were then resuspended in 500 ml infiltration medium (autoclaved 5% sucrose) and 250 µl/L Silwet L-77™ (84% polyalkyleneoxide modified heptamethyltrisiloxane and 16% allyloxypolyethyleneglycol methyl ether), and transferred to a one liter beaker.

The previously clipped Arabidopsis plants were dipped into the Agrobacterium suspension so that all above ground parts were immersed and agitated gently for 10 seconds. The dipped plants were then covered with a tall clear plastic dome to maintain the humidity, and returned to the growth room. The following day, the dome was removed and the plants were grown under normal light conditions until mature seeds were produced. Mature seeds were collected and stored desiccated at 4° C.

Transgenic Arabidopsis T1 seedlings were selected. Approximately 70 mg seeds from an agrotransformed plant were mixed approximately 4:1 with sand and placed in a 2 ml screw cap cryo vial. One vial of seeds was then sown in a cell of an 8 cell flat. The flat was covered with a dome, stored at 4° C. for 3 days, and then transferred to a growth room. The domes were removed when the seedlings first emerged. After the emergence of the first primary leaves, the flat was sprayed uniformly with a herbicide corresponding to the chemical resistance marker plus 0.005% Silwet (50 µl/L) until the leaves were completely wetted. The spraying was repeated for the following two days.

Ten days after the first spraying resistant plants were transplanted to 2.5 inch round pots containing moistened sterile potting soil. The transplants were then sprayed with herbicide and returned to the growth room. The herbicide resistant plants represented stably transformed T1 plants.

EXAMPLE 5

Effect of SAT Antisense Expression in Arabidopsis Seedlings

The T1 SAT antisense target plants from the transformed plant lines obtained in Example 4 were crossed with the Arabidopsis transgenic driver line described above. The resulting F1 seeds were then subjected to a plate assay to observe seedling growth over a 2-week period. Seedlings were inspected for growth and development. Antisense expression of the SAT gene in one line resulted in reduced growth and unusual pigmentation in four of seven seedlings indicating that the SAT gene is essential for normal plant growth and development.

EXAMPLE 6

Cloning, Expression, and Purification of the SAT Protein

The following protocol was employed to obtain purified SAT protein.

Cloning, Expression and Purification of a SAT protein:

Total RNA was collected from 14-day-old *Arabidopsis thaliana* seedlings using published protocols, and reagents (Trizol) from Life Technologies, Inc. (Rockville, Md.). One µl of 10 µM custom oligo, GCT CGC GGC CGC TTA TAT GAT GTA ATC TGA (SEQ ID NO:9), was incubated with 1 µg of total RNA in a reverse transcriptase polymerase chain reaction (RT-PCR) (Invitrogen kit) according to the manufacturer's recommendations. The SAT cDNA was then selectively amplified by PCR with the primer pair ATT GGT ACC ATG CCA CCG GCC GGA GAA (SEQ ID NO:10) and GCT CGC GGC CGC TTA TAT GAT GTA ATC TGA (SEQ ID NO:11). The resulting PCR product encoding SEQ ID NO:2, and plasmid pET30c(+) (Novagen, Madison, Wis.) were digested with restriction endonucleases KpnI and NotI as directed by the manufacturer (New England Biolabs, Beverly, Mass.). Ligation of these two linear DNAs into the resulting recombinant clone pET30c-SAT was accomplished by following instructions included with T4 DNA ligase (New England Biolabs). The integrity of the above clone was verified by DNA sequence analysis to confirm the sequence set forth in SEQ ID NO:3.

Clone pET30/SAT was transformed into the Rossetta *E. coli* bacterial strain (Novagen) following the manufactures instructions. Transformed bacteria were grown in LB liquid media containing 50 µg/ml kanamycin and 35 µg/ml chloramphenicol to an optical densitiy of ~0.6 at 600 nm. At that point, isopropylthio-Beta-galactoside (IPTG) was added to a final concentration of 1 mM, and the culture was incubated at room temperature overnight. Cultures were pelleted by centrifugation, and the cell pellets were stored at −80° C. Pellets from ~500 mls of culture were lysed in 20 ml of Bugbuster lysis solution (Novagen) with 20 µl of benzonase following the manufactures suggested protocol. The lysis was clarified by centrifugation at 15,000×g for 10 minutes. Collected supernate contained soluble SAT fusion protein (SEQ ID NO:4), as determined by Coomossie and western blot analysis. Purification using Ni affinity resulted in an SAT preparation of ~90% purity when analyzed by SDS-page.

What is claimed is:

1. A method for identifying a compound as a candidate for a herbicide, comprising:

a) measuring the enzymatic activity of a SAT polypeptide having at least 10% of the activity of SEQ ID NO:2 in the presence and absence of a compound, wherein a decrease of the SAT polypeptide enzymatic activity in the presence of the compound indicates the compound as a candidate for a herbicide.

2. The method of claim 1, wherein the SAT polypeptide is a plant SAT polypeptide.

3. The method of claim 2, wherein the plant is a dicot.

4. The method of claim 2, wherein the plant is a monocot.

5. The method of claim 2, wherein the plant is other than a C3 plant.

6. The method of claim 2, wherein the plant is other than a C4 plant.

7. The method of claim 1, wherein the SAT polypeptide is SEQ ID NO:4.

8. A method for identifying a compound as a candidate for a herbicide, comprising:

a) contacting a SAT polypeptide having at least 10% of the activity of SEQ ID NO:2 with acetyl-CoA and L-serine in the presence and absence of a compound or contacting a SAT polypeptide with O-acetyl-L-serine and CoA in the presence and absence of a compound; and b) determining a change in concentration for at least one of acetyl-CoA, L-serine, O-acetyl-L-serine and/or CoA in the presence and absence of the compound, wherein a change in the concentration for any of acetyl-CoA, L-serine, O-acetyl-L-serine and/or CoA indicates that the compound is a candidate for a herbicide.

9. The method of claim 8, wherein the SAT polypeptide is a plant SAT polypeptide.

10. The method of claim 9, wherein the plant is a dicot.

11. The method of claim 9, wherein the plant is a monocot.

12. The method of claim 9, wherein the plant is other than a C3 plant.

13. The method of claim 9, wherein the plant is other than a C4 plant.

14. The method of claim 8, wherein the SAT polypeptide is SEQ ID NO:4.

* * * * *